(12) United States Patent
Erkkila et al.

(10) Patent No.: US 9,760,692 B2
(45) Date of Patent: Sep. 12, 2017

(54) DISPLAYING EXERCISE DATA

(71) Applicant: Polar Electro Oy, Kempele (FI)

(72) Inventors: Mika Erkkila, Oulu (FI); Ville Kampman, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 369 days.

(21) Appl. No.: 14/031,768

(22) Filed: Sep. 19, 2013

(65) Prior Publication Data

US 2015/0081055 A1    Mar. 19, 2015

(51) Int. Cl.
*A63F 13/211* (2014.01)
*G06F 19/00* (2011.01)

(52) U.S. Cl.
CPC .............. *G06F 19/3481* (2013.01)

(58) Field of Classification Search
CPC ...... A63B 24/0084; A63B 71/06; G06F 19/00
USPC ............. 463/40–42, 46, 47; 700/91
See application file for complete search history.

(56) References Cited

U.S. PATENT DOCUMENTS

| | | | | |
|---|---|---|---|---|
| 9,392,941 | B2* | 7/2016 | Powch | A61B 5/02055 |
| 2012/0078396 | A1* | 3/2012 | Case, Jr. | A63B 24/00 |
| | | | | 700/91 |
| 2012/0203360 | A1* | 8/2012 | Tagliabue | A63B 24/0084 |
| | | | | 700/91 |
| 2012/0283855 | A1* | 11/2012 | Hoffman | G01C 21/20 |
| | | | | 700/91 |
| 2015/0185991 | A1* | 7/2015 | Ho | G06F 3/0484 |
| | | | | 715/771 |

FOREIGN PATENT DOCUMENTS

| | | |
|---|---|---|
| WO | WO2006065679 A2 | 6/2006 |
| WO | WO2006065679 A3 | 6/2006 |
| WO | WO2012021507 A2 | 2/2012 |
| WO | WO2012021507 A3 | 2/2012 |

OTHER PUBLICATIONS

Two Brand-New Apps to Match Your Music With Your Pace on Your Next Run by Amanda McMillian, posted Jun. 19, 2013.*
"Automatic Speed Based Volume Control of your Iphone" posted on May 29, 2013.*
"Facebook Groups Let You See Exactly Who Has Viewed Your Photos, Too" by Ingrid Lunden posted Aug. 11, 2012.*
European Search Report for corresponding European Application No. EP 14 18 5353, pp. 1-3 (dated Aug. 19, 2015).

* cited by examiner

*Primary Examiner* — David L Lewis
*Assistant Examiner* — Ross Williams
(74) *Attorney, Agent, or Firm* — Hoffmann & Baron, LLP

(57) ABSTRACT

There is provided a server computer system configured to acquire recorded exerise data of an exercise performed by an exeriser; acquire recorded location data of the exercise, wherein the location data depicts a route travlled during the exerise; acquire a map of an area which comprises the trivlled route; generate the dynamic execise presentation on the basis of the exercise data andthe location data, wherein the dynamic exercise presentation comprises: displaying the exercise data as a function of the location data on a display having the map as a background, and automatically moving a pointer on the display along the traveled route on the basis of the location data such that the moving pointer depocts the location of the exerciser on the travlled route as the exercise advances; and cause a display of the exercise presentation on the display via a network.

17 Claims, 5 Drawing Sheets

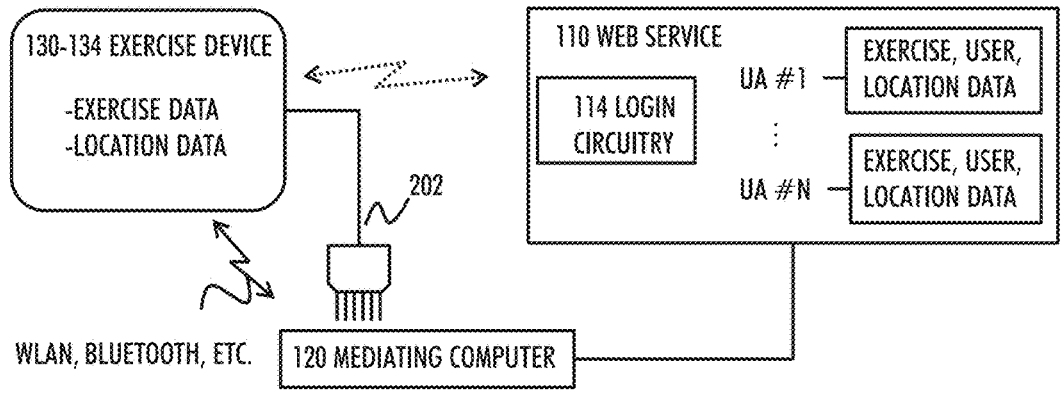
FIG. 2
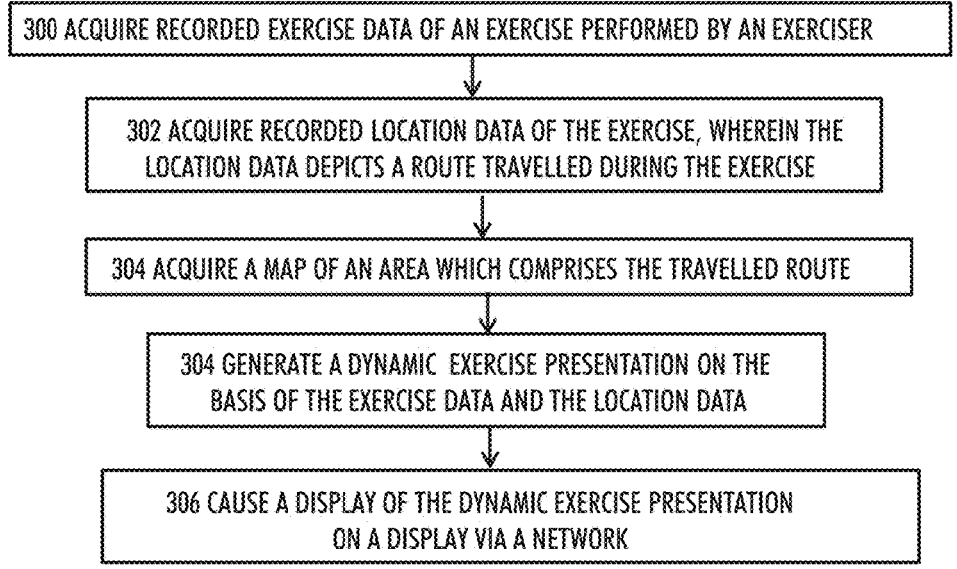
FIG. 3
| LOCATION DATA | HEART ACTIVITY DATA | TIME | DISTANCE | ... | CALORIES |
|---|---|---|---|---|---|
| X1, Y1, Z1 (START) | HR 1 | T 1 | D 1 | | CAL 1 |
| X2, Y2, Z2 | HR 2 | T 2 | D 2 | ... | CAL 2 |
| ... | ... | ... | ... | | ... |
| XN, YN, ZN (END) | HR N | T N | D N | | CAL N |
FIG. 4

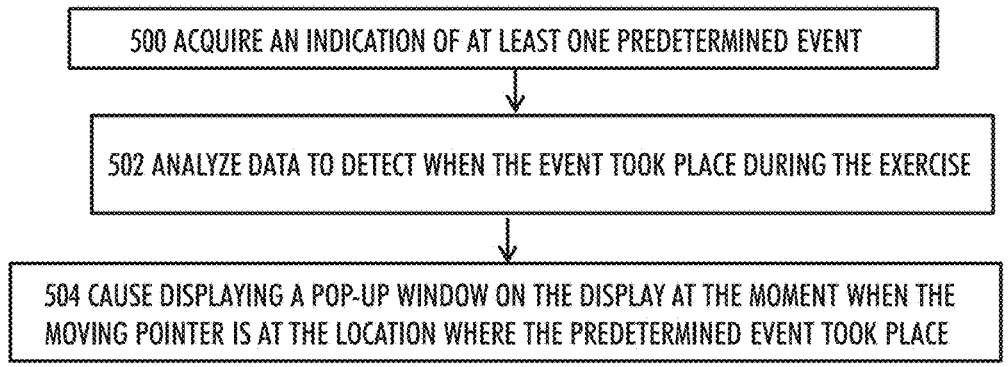

DISPLAYING EXERCISE DATA

BACKGROUND

Field

The invention relates generally to generating an exercise presentation of a recorded exercise and displaying the exercise presentation.

Description of the Related Art

Nowadays people like to analyze their training data afterwards via a display, such as a computer screen. However, the current way of showing the information of a training event (which may have a considerable length) to the viewer does not illustrate the training data in a clear, readily understandable manner. Furthermore, the traditional presentation of recorded training data using static graphs, bars and texts is considered as rather serious and not entertaining. Therefore, an improved manner of showing the training data is needed.

SUMMARY

According to an aspect of the invention, there is provided an apparatus as specified in claim 1.

According to an aspect of the invention, there is provided a method as specified in claim 19.

According to an aspect of the invention, there is provided a computer program product as specified in claim 20.

According to an aspect of the invention, there is provided a computer-readable distribution medium carrying the above-mentioned computer program product.

According to an aspect of the invention, there is provided an apparatus comprising means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which

FIG. 2 shows how data may be transferred to a web service, according to an embodiment;

FIG. 3 shows a method, according to an embodiment;

FIG. 4 illustrates a table for mapping exercise data and location data, according to an embodiment;

FIG. 5A depicts a method, according to an embodiment;

FIG. 5B illustrates a user interview of the web service, according to an embodiment.

DETAILED DESCRIPTION

Figure 1:
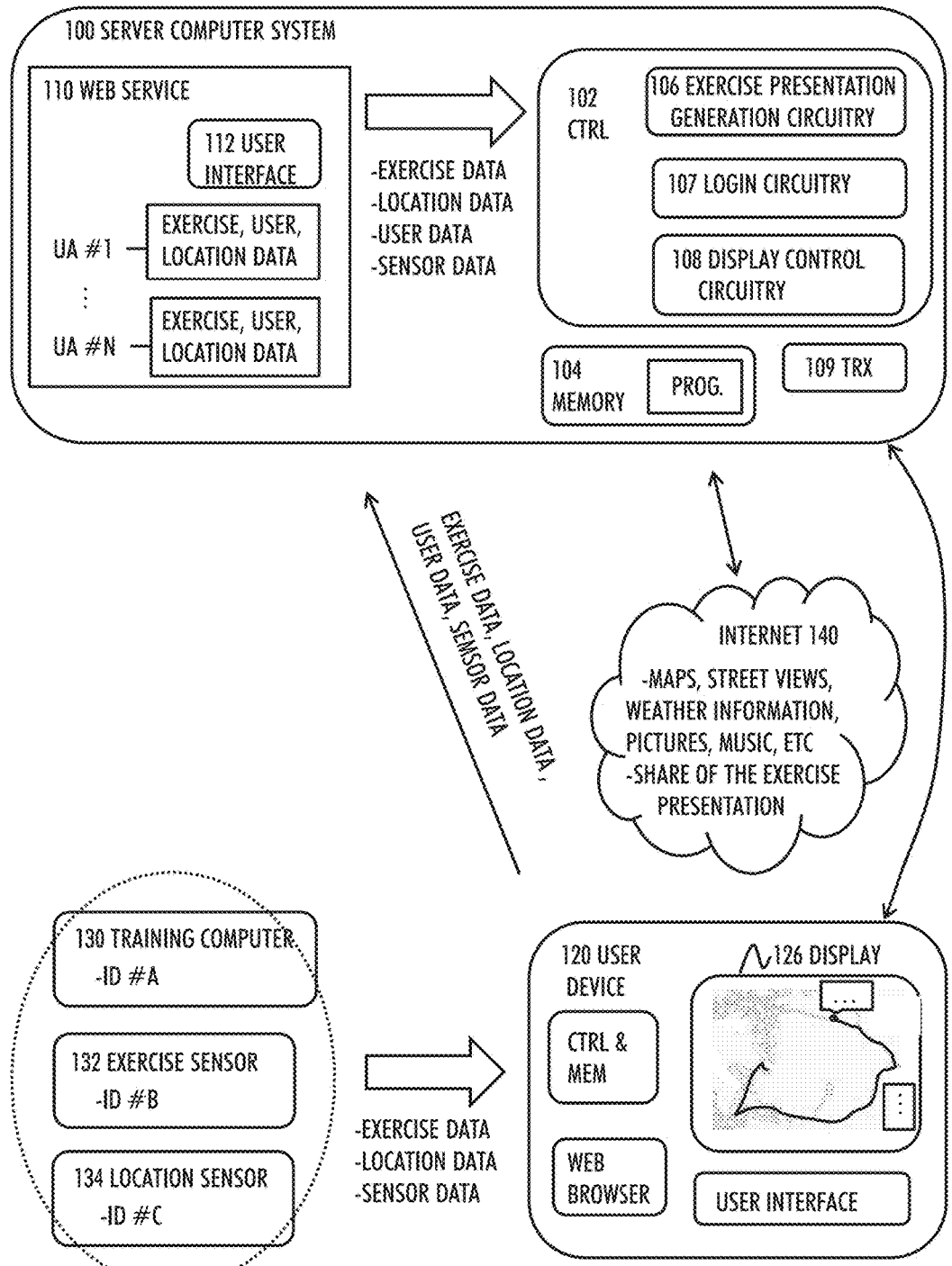
FIG. 1 presents a system, according to an embodiment.

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

It is common to wear a personal training computer (TC) 130 during an exercise. The TC 130 may be a wrist worn device or a chest worn device, for example. The exerciser may monitor exercise data of the exerciser, such as heart activity data, from the TC 130 during the exercise in real time. This may take place by the training computer 130 receiving information from an exercise sensor 132, 134, such as heart rate-related information from a heart rate sensor, location specific information from a foot pod or from a global positioning system (GPS) receiver, cadence data from a corresponding monitoring device, pace/speed related data from the GPS/foot pod, etc. In an embodiment, the sensor 132, 134 is integrated into the TC 130. The training computer 130 may store the data as exercise data which the user (exerciser) may use in post-analysis of the performed exercise. In an embodiment, the post-analysis is processed in the TC 130. In another embodiment, the exercise data are transferred from the training computer 130 and/or exercise sensor 132, 134 to a web service 110 located in a server of a network, and the post-analysis is carried out in the web service 110.

Such web service 110 may comprise exercise data user accounts (UA), each exercise data user account comprising exercise data associated with a specific user. As such, there may be different user accounts for different users #1, #2, . . . , and #N. An example of such a web service 110 may be a Polar Personal Trainer (PTT), Polar Flow or iFIT service which comprises a database for storing the plurality of user accounts. It should be noted that the web service 110 and the user accounts may be stored on a same or on different server computers, which may be comprised in a same server computer system. The web service 110 may be identified with a static or dynamic uniform resource locator (URL) in the Internet.

The end users, or exercisers, may upload their training/exercise data from their exercise sensors 132, 134 or training computers 130 to the corresponding user accounts, or feed data manually to the web service 110. In an embodiment, the web service 110 may require that the users first connect to the web service 110 by applying a user name and a password, or other identification means. For such purpose, the SCS 100 may comprise a login circuitry 107 which may be responsible of authentication the users trying to access the web service 110. Once allowed by the login circuitry 107, the user may transfer, e.g., training data from their exercises devices 130-134 to the user accounts. The user may also change the settings of his/her exercise device(s) 130-134 in the web service 110 and download the exercise device's settings from the web service 110 via the network to the exercise device 130-134.

As shown in FIG. 2, the transfer of the exercise data from the exercise device(s) 130 to 134 may be performed wirelessly (e.g. WiFi, Bluetooth, Bluetooth low energy (BLE), infra-red, cellular network connection, etc.) or via a wire (e.g. universal serial bus 202) to a user device 120, or to any mediating computer, which is used in accessing the web service 110 in the network. However, in one embodiment, the exercise device 130 to 134 may access the web service 110 directly (e.g. wirelessly). As such, the exercise data may be stored in the user's user account within the web service 110 so that the user may later analyze and view his/her exercise data, for example.

The training/exercise data, also known as physiological sensor data or exercise-related data, at the user accounts may have been stored during/after one exercise or during several exercises or physical activities and comprise training history including measurement data and accumulated exercise data. The user accounts may additionally store physiological data of the user and user attributes obtained from the exerciser and/or the exercise device, such as name, gender, age, weight, height, image, status, motto, fitness level, training schedule, maximum oxygen intake (VO2Max), maximum heart rate (HRMax), performance zones (heart rate zones, speed zones), aerobic and anaerobic thresholds. The user related data, such as the name or any of the other data items listed, may be used as a user identifier of the user of the exercise device. As such, user records may be transferred from the exercise devices 130-134 to the web service 110 and to corresponding user accounts.

The exerciser may then wish to analyze his/her exercise/training data from a display, such as from the display 126 of the user device 120, which is connected to the web service 110 via the network. The exercise data may be displayed in the display 126 in various manners, including time stamped values of the recorded exercise data or route being showed on a map layout, for example. However, the current ways of displaying the data to the exerciser are cumbersome to quickly understand by the exerciser. Furthermore, the current way of presenting the recorded exercise is not entertaining and, thus, people may find it not interesting to watch.

Therefore, in order to tackle at least the above mentioned drawbacks of the current way of showing a recorded exercise, there is provided, as shown in FIGS. 1 and 3 a server computer system (SCS) 100 for generating a dynamic exercise presentation of a recorded exercise. The server computer system may comprise one or more server computers 100, which may or may not share the execution of the functionalities of the server computer system 100. The SCS 100 may be caused to automatically generate the dynamic exercise presentation or it may generate the exercise presentation only upon request, such as a request from the exerciser (i.e. the user of the user device 120) via the web service 110. The SCS 100 may comprise at least one processor 102 and at least one memory 104 including a computer program code.

The at least one memory 104 and the computer program code are configured, with the at least one processor 102, to cause the SCS 100 at least to acquire, in step 300, the recorded exercise data of the exercise performed by the exerciser, and further, in step 302, to acquire recorded location data of the exercise, wherein the location data depicts a route traveled during the recorded exercise. The following is a non-limiting list of possible types of exercise data: heart rate zones, heart rate samples, heart rate variation samples, heart beat interval samples, fat consumption value, calorie consumption value, activity zones, activity samples, speed and/or pace samples, power samples, cadence samples, altitude samples, temperature samples, location samples, distance elapsed, time elapsed, pedal index, left-right balance, running index, training load, galvanic skin response samples, fluid balance, skin temperature samples and/or heading samples. The location data may comprise satellite positioning data, such as, GPS positioning data, or any other data that allows the determination of the location of the exerciser during the exercise at any given time. The movement indoors may be detected via indoor location tracking methods, such as mapping techniques including measuring Earth's magnetic fields or radio frequency signals. It may be noted that the exercise which is to be presented may have comprised movement of the exerciser along the route. The route may comprise indoor or outdoor parts or it may be performed solely either indoors or outdoors. The route may be short (such as few meters) or long (such as many kilometers). The recorded exercise may have comprised walking, running, skiing, skating, bicycling, driving, or any other activity in which the exerciser moves and thus forms a traveled route.

As shown in FIG. 1, the SCS 100 may apply the exercise and location data stored in the web service 110 and, more particularly, in a user account corresponding to this exerciser. For example, the exercise and location data is automatically accessed and applied by the SCS 100 for the purpose of generating the exercise presentation, upon detecting that the exercise and location data has been transferred from the exercise devices 130-134 to the web service 110.

In an embodiment, the SCS 100 provides the web service 110, as shown in FIG. 1. In such case, no transfer of exercise and location data via the network needs to take place but the SCS 100 may apply and access the exercise and location data in the web service 110 internally. However, in another embodiment, a server providing the web service 110 and the SCS 100 are different entities, connected to each other via the network (e.g. Internet). In such embodiment, the SCS 100 may download the exercise and location data from the web service 110 and, more particularly, from the user account corresponding to this exerciser. In both cases, the SCS 100 acquires the recorded exercise data and the recorded location data of the performed exercise.

In step 304, the SCS 100 may acquire a map of an area which comprises the traveled route. In case of outdoor sports, the satellite positioning coordinates may imply the geographical map area which comprises the route. In case of indoor sports, the floor plan of the building may serve as the map. As shown in FIG. 1, the SCS 100 may fetch the map from a database in the internet 140. An example database may be a Google maps—database. Alternatively, the exerciser may upload the map of the area.

Thereafter, in step 306, the SCS 100 may generate the dynamic exercise presentation on the basis of the exercise data and the location data. In step 308, the SCS 100 may cause a display of the exercise presentation on a display via the network. The display on which the exercise presentation is displayed may be, for example, the display 126 of the user device 120. The user device 120 may be a home computer, a tablet, or a smart phone, for example. The request may be received from the owner of the user device 120 (e.g. from the exerciser). Additionally, as will be explained later, the dynamic exercise presentation may be shared on the internet 140 and viewed by a third party at his/her user terminal/device upon a request from the third party. Displaying the exercise presentation may be automatic or executed only upon request. Such request may be acquired from the user terminal 120 over the network, for example. In an embodiment, the request may be made to the web service 110 via the user interface 112 projected on the user's terminal 12, for example.

FIG. 4 illustrates how the location data and the exercise data may be mapped together. FIG. 4 uses a table for illustrative purposes. For each data unit on the column of the location data, there may be a counterpart data unit on at least one column of the exercise data. In this example illustration, the recorded exercise data indicates at least heart rate, elapsed time, elapsed distance and consumed calories. As shown, in the start coordinates X1, Y1, and Z1 (corresponding to 3-dimensional coordinate axis, where Z may be the altitude of the exerciser during the route), the heart rate is HR1, elapsed time is T1 (=0 seconds), elapsed distance is D1 (=0 meters) and the amount of consumed calories is CAL1 (=0 calories). In location data coordinates X2, Y2, Z2, the corresponding, non-zero values are HR2, T2, D2, and CAL2. In this way, the SCS 100 may know, for each location data unit (i.e. for each location on the route), the corresponding exercise data values. It may be noted that the SCS 100 may also apply the location data in order to derive some of the exercise data values, such as the elapsed distance.

Let us look further on what the dynamic exercise presentation comprises. In an embodiment, the dynamic exercise presentation comprises displaying the exercise data as a function of the location data on the display (e.g. on the display 126) having the fetched map as a background. An example exercise presentation is shown in FIGS. 6A-6D. As shown, the geographical map of an area comprising the traveled route may serve as the background for the presentation. The scale of the map may be automatically matched such that the traveled route is clearly illustrated in the presentation. Alternatively, the scale may be selected by the exerciser through an application user interface 112 of the web service 110. Similarly, the amount of details, such as altitude contours, may be selected by the exerciser (i.e. the user of the user device 120).

An example illustration of the user interface 112 is shown in FIG. 5B. However, it should be noted that the user interface 112 may comprise more options than the ones shown in FIG. 5B, which comprises, for the sake of clarity, only some example options.

In an embodiment, the dynamic exercise presentation is divided into multiple parts, similarly as in a movie. The parts may comprise a start part, an action part, and an end part. The start part may comprise playing music or audio in the beginning. The exerciser may itself select the music to be played by uploading music files to the SCS 100, or the exerciser may let the SCS 100 apply a preconfigured music/audio file. Further, in the start part, the name of a studio or a production company offering the presentation, e.g. Polar Electro, may be presented. In an embodiment, the start part includes advertising material selected by the user. In the start part, the type of sport to be presented (running, bicycling, etc.) may be illustrated. In the action part, the recorded exercise may be dynamically shown to the viewer, as will be described below. The action part may be started by illustrating the location of the recorded training data, wherein the detection of the location may be automatically based on the location data. This may be represented, e.g. by displaying the location as text (e.g. Oulu, Finland), a map or a satellite picture zooming into the detected location. In the end part, a summary of the exercise may be given, as will be described later.

Let us now take a look at the dynamic exercise presentation in more details. At least some of the exercise data may be shown on the display 126 as a function of the location data. This may take place with a dedicated exercise data window 600 (as is the case in FIG. 6). In another embodiment, some exercise data, such as the heart rate in beats per minute (BPM), may be given as color indicators. For example, the traveled route may be illustrated with different colors, wherein the color of the route at a particular point depicts the heart rate or heart rate zone of the exerciser at that point of the route during the recorded exercise. Some exercise data, such as altitude of the exerciser during the exercise may be given in a Z axis, for example.

In an embodiment, the exerciser may select, through the user interface 112 of the web service 110, which type of exercise data is to be shown on the display 126, such as in the window 600. That is, the SCS 100 may be caused to display the user interface 112 on the display 126 so that the SCS 100 may receive commands from the user via the user interface 112. In an embodiment, the type(s) of exercise data shown on the display 126 depends on the location of the exerciser on the route (that is, as a function of the location data). As shown in FIG. 6, the values of the type(s) of exercise data depends on the location data and, thus, on the location of the exerciser on the route. For example, the displayed heart activity data may vary according to the heart rate of the exerciser during the exercise.

In an embodiment, the SCS 100 is caused to automatically move a pointer 602 on the display 126 along the traveled route on the basis of the location data such that the moving pointer 602 depicts the location of the exerciser on the traveled route as the recorded exercise advances. Thus, the location of the exerciser on the route is shown dynamically on the display 126 with the pointer 602. The pointer may be of any form, although depicted with a circle in the FIGS. 6A-6D. Such presentation of the position of the exerciser provides an easily understandable way of indicating where the exerciser was at a certain time during the exercise. Further, the viewer may easily see how fast the person is moving in a given part of the route. As the map background may comprise, e.g., altitude contours, the viewer may easily see how an uphill, for example, affects the persons speed, or which part of the route cause is the fastest and which one is the slowest.

In an embodiment, the exercise presentation further comprises displaying the traveled route on the display 126 cumulatively as the moving pointer 602 moves on the traveled route. For example, looking at FIG. 6A, the traveled route is not shown at all because the moving pointer 602 is at the start of the exercise. As the exercise evolves in FIGS. 6B-6D, the route becomes dynamically shown on the display 126. At the end of the route (FIG. 6D), the whole route is finally shown. This provides excitement for the viewer as then the viewer does not know beforehand where the exerciser will turn in a given intersection. However, in another embodiment, the whole route is shown already in the beginning in which case the pointer 602 moves along the already fully displayed route.

In an embodiment, the moving pointer 602 is associated with a window for showing at least some of the exercise data, wherein the exercise data to be shown on the window is based on the location data. An example window is shown in FIGS. 6A to 6D with the window 600. However, in an embodiment, there is instead or additionally an exercise data window moving along with the moving pointer 602, although not shown in FIGS. 6A-6D. As the moving pointer 602 moves, the content of the exercise data window may change according to the location of the moving pointer (i.e. according to the position of the exerciser during the recorded exercise). In an embodiment, by varying content it is meant that the type(s) of exercise data shown may vary as the pointer 602 moves. The SCS 100 may further receive instructions over the network from the exerciser, wherein the instructions determine which type(s) of exercise data is to be shown on the window. For example, the exerciser may select that the window is to display heart activity data, elapsed time and elapsed distance.

In an embodiment, as shown in FIG. 5A, the SCS 100 is caused, by the at least one memory 104, the computer program code and the at least one processor 102, to acquire an indication of at least one predetermined event in step 500. This acquisition may be obtained from the exerciser over the network, for example, or from a third party desiring to view a shared exercise presentation. As shown in FIG. 5B, the user may use a mouse or touch display to tick one or many of the possible events which are to be highlighted during the exercise presentation. In yet one embodiment, the event(s) may be preconfigured to the SCS 100 by system manager or programmer. A non-limiting list of example events (i.e. exercise highlights) may include at least one of: start of the exercise, the maximum heart rate during the exercise, the maximum speed or pace during the exercise, the highest elevation (altitude) during the exercise, the maximum running or cycling cadence during the exercise, the maximum running or cycling power during the exercise, the fastest part of the exercise (e.g. fastest kilometer, fastest mile), the steepest incline during the exercise, end of the exercise, a user specified location. In an embodiment, the highlights may be personal highlights.

In step 502, the SCS 100 may analyze one of the recorded exercise data, the recorded location data, and/or user instructions, in order to detect from the exercise data when the predetermined event took place during the exercise. For example, when the maximum heart rate is ticked to be one of the at least one exercise events, the SCS 100 may go through the exercise data in order to find the maximum of the heart rate values. Then the SCS 100 may check in what point of the traveled route the maximum heart rate took place by analyzing the location data units together with the exercise data units. This may take place by analyzing the table of FIG. 4, for example. In an embodiment, however, the predetermined event is not calculated based on the exercise or location data, but the predetermined event is set by the exerciser to highlight, for example, a great view or a special location. Such setting may be given manually by the exerciser by ticking a certain point on the traveled route, or by allowing the SCS 100 to browse through street views associated to the traveled route and to determine automatically which street views comprise great landscapes, for example.

In step 504, the SCS 100 may then cause displaying a pop-up window 604 on the display at the moment when the moving pointer 602 is at the location of the traveled route where the predetermined event took place. In an embodiment, the point of the traveled route, where the predetermined event took place, is shown on the display before the moving pointer 602 reaches that point of the traveled route. For example, an indicator may emerge at the point of the traveled route where the event took place before the moving pointer 602 reaches that point. The indicator may be, e.g., a blinking light. In an embodiment, all the points of the traveled route where at least one predetermined event takes place are shown in advance at the start of the exercise presentation. In another embodiment, the locations in which the predetermined events take place are indicated only as the pointer 602 reaches that point along the traveled route. However, in one embodiment, no event is selected and the exercise presentation comprises no pop-up windows 604.

The pop-up window 604 may comprise exercise data which is shown to the viewer for certain duration of time, as illustrated in FIGS. 6A-6D. The durations for the pop-up windows 604 may be determined individually by the exerciser through the user interface 112 of FIG. 5B. In another embodiment, each pop-up window 604 has the same duration. In an embodiment, the duration is between one and four seconds. In an embodiment, during the period when the pop-up window 604 is on the display 126, the moving pointer is not moving. In other words, the exercise is not progressing (is paused) on the display 126 during that time.

It may be noted also, that in an embodiment, the pop-up for a certain event may comprise not only one point in the route, but a part of the route. This may be the case, e.g., when the predetermined event is the fastest kilometer. In such case, the pop-up window 604 may be displayed for the whole kilometer as the moving pointer 602 moves on the part of the route corresponding to the fastest kilometer. In such case, the progress of the exercise need not be paused for the duration of the pop-up window 604 display.

Figure 6A:
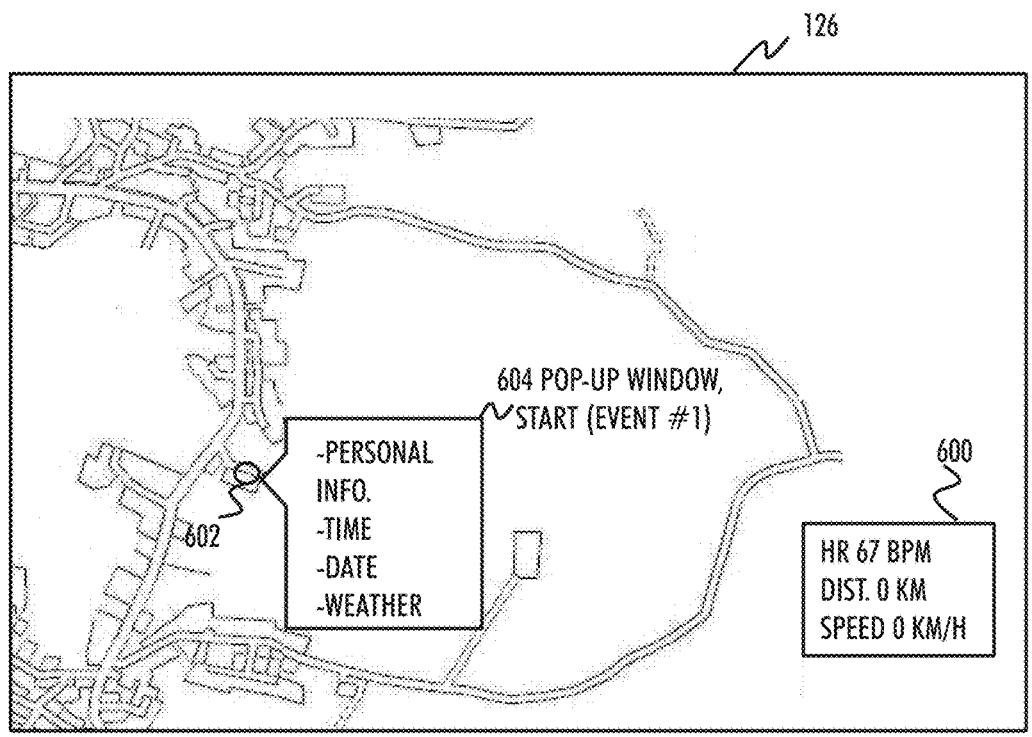
FIGS. 6A to 6D show an example exercise presentation.
Figure 6B:
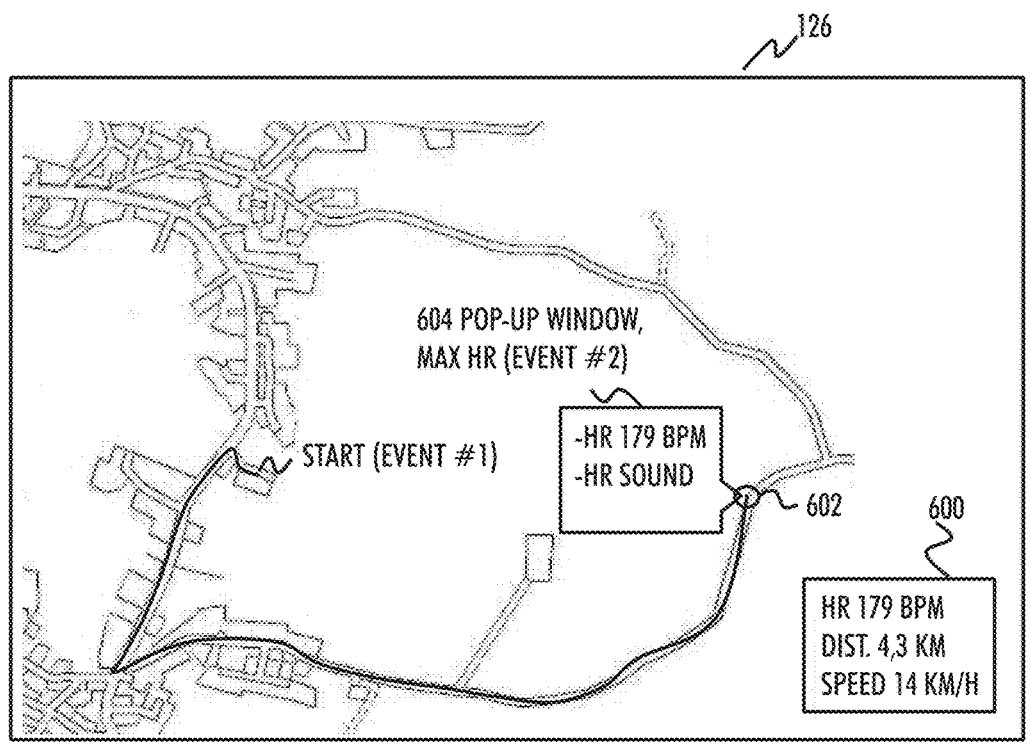

In an embodiment, each predetermined event is associated with a dedicated pop-up window 604. This is shown in FIG. 5B in which each row, corresponding to one predetermined event, comprises a dedicated pop-up window which is to be used in association with the event on that row. Further, in an embodiment, the content of the dedicated pop-up window 604 may depend on the predetermined event which is associated to that pop-up window. For example, a pop-up window 604 for the maximum heart rate may have content according to which an audio file is to be outputted through speakers and the current (maximum) heart rate is to be shown on the pop-up window 604. This is shown in FIGS. 5 and 6B.

In an embodiment, the content of the dedicated pop-up window 604 is predetermined on the basis of the associated event. However, in an embodiment, the SCS 100 is further receives an indication of required content of a particular pop-up window 604 associated with a particular predetermined event, and to modify that pop-up window for this particular predetermined event on the basis of the indication. This may be beneficial in that the exerciser, for example, may modify each pop-up window 604 as he/she desires. The exerciser may e.g. determine that the pop-up window 604 associated with maximum heart rate comprises a link to an internet address which explains the physiological effects of such a high heart rate. The exerciser may modify the desired content of any of the pop-up windows 604 through the user interface 112 of FIG. 5B, for example.

In an embodiment, the pop-up window 604 comprises audio output, such as music. In an embodiment, the output of audio during a particular pop-up window comprises outputting a sound of a heart beating according to the heart rate of the exercises at the location of the traveled route in which the particular pop-up window 604 is displayed. The SCS 100 may check what the heart rate of the exerciser at that location of the route is, and modify the beat of a prerecorded heart beat sound to correspond to the heart rate of the exerciser, for example. The prerecorded heart rate sound may or may not correspond to the exerciser himself/herself. There may be an option in the user interface 112 which the exerciser may choose in order to request the SCS 100 to play the heart beat sound.

Figure 6C:
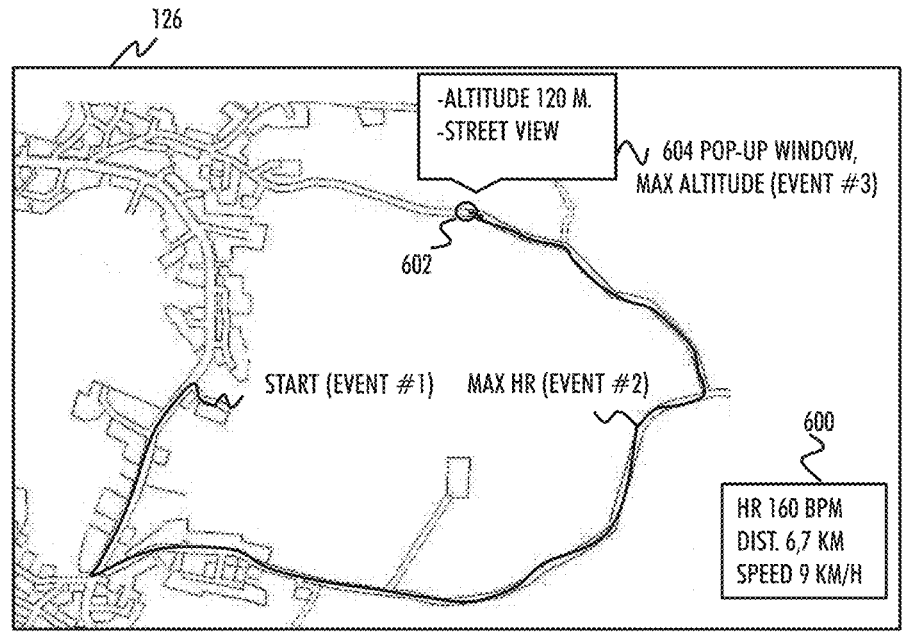

In an embodiment, the SCS 100 may acquire an indication that a pop-up window 604 for a particular predetermined event is to include a street view corresponding to the location on the traveled route in which the particular predetermined event took place. The exerciser may give the indication, e.g., through the user interface 112 of FIG. 5B by clicking a corresponding option. In the example of FIGS. 5B and 6C, the street view is comprised in the pop-up window 604 associated with the highest elevation point on the route. The street view should be understood broadly to cover also indoor views, landscapes, etc. The SCS 100 may analyze the acquired location data to find where the highest location on the route is, and then check the XYZ-coordinates for that location.

Then the SCS 100 may automatically fetch the street view from the network. The correct street view may be selected on the basis of XYZ location coordinates. The database used for fetching the picture/video from the network may be the database applied by Google Maps® of Google StreetView®, or any other database for storing pictures/videos of outdoor or indoor locations. In another embodiment, the exerciser may upload his/her pictures/videos by clicking the corresponding option in the user interface 112. The street view may comprise panorama pictures, normal pictures, or videos (such as a video comprising a 360 degrees rotation), to mention only a few possible options. The street view may be towards the movement of the exerciser on the traveled route. In this way, the exercise presentation of on-place pictures, like Google StreetView, may be done by showing the entire 360 degrees picture or parts of it, based on the direction detected from the recorded data in relation to view of the virtual camera point.

Thereafter, the SCS 100 may include the fetched street view to the corresponding pop-up window 604. For example, during the exercise presentation, the pop-up window 604 with the fetched street view may be displayed when the moving pointer 602 is at the location of the particular predetermined event on the traveled route. This may further improve the user experience of viewing the recorded exercise. In one embodiment, the view may follow the recording's direction, wherein the video may start to play a predefined time/distance before the point of the predetermined event at the route and continue until a predefined time/distance after the highlight.

In an embodiment, the SCS 100 may acquire an indication that a particular pop-up window 604 for a particular predetermined event is to include a link to an internet address. The exerciser may give such indication of a specific internet address or addresses, e.g., through the user interface 112 of FIG. 5B. Then, the SCS 100 may include the internet address to the particular pop-up window 604. During the exercise presentation, the pop-up window 604 with the internet address may be popped up when the moving pointer 604 is at the location of the particular predetermined event on the traveled route. If the viewer of the exercise presentation clicks on the link to the internet address, the viewer is directed automatically to the website of the internet address. During the exerciser browses the website, the exercise presentation may be paused. Such use of links to certain internet addresses may be beneficial for the viewer to acquire more relevant information related to the exercise, for example.

In an embodiment, the SCS 100 may acquire an indication that a pop-up window for a predetermined event is to comprise content from an indicated internet protocol address. The exerciser may give such indication of the content and the specific IP address or addresses, e.g., through the user interface 112 of FIG. 5B. Then the SCS 100 may fetch the content from the indicated internet protocol address and include the content to the pop-up window 604. Thereafter, during the dynamic exercise presentation, the pop-up window 604 with the content may be displayed when the moving pointer is at the location of the particular predetermined event on the traveled route.

In an embodiment, the SCS 100 may acquire personal information of the exerciser from the exercise data user account of the web service 110. Such personal information may comprise name (or other identifier), age, height, weight, person or avatar picture, person's status or motto, for example, as partly shown in the user interface 112 of FIG. 5B. Then, at least at some point of the exercise presentation, the personal information is displayed. In an embodiment, the personal information may be given at the beginning of the exercise (e.g. in the start part), as shown in FIG. 6A, possibly in a pop-up window 604. The personal information may be shown also in other parts of the exercise presentation (i.e. in the action part and/or in the end part).

In an embodiment, the SCS 100 may acquire information of the at least one sensor 132, 134 used for recording the exercise data and/or location data during the exercise. The information of the sensors 132, 134 may be obtained from the user's account of the web service 110. These sensors may comprise GPS receivers, radio frequency signal receivers, training computers, heart activity sensors, foot pods, pedaling sensors, to mention only a few possible types of exercise devices 130-134 of FIG. 1. Thereafter, the dynamic exercise presentation may comprise displaying at least some of the information of the at least one sensor on the display 126. For example, in the beginning or at the end of the exercise presentation, the exercise device 130-134 used for recording the data may be identified and showed. For example, the display 126 may read "Polar Beat with Polar H7" as a training gear used to record at least some of the data that is presented to the viewer. Further, other training gear used at training, such as the brand, model and/or type of the clothes or shoes, may be illustrated.

In an embodiment, the SCS 100 may show sensor images/pictures fetched from the internet 140 or from the corresponding user's account of the web service 110. Such fetching of images may be dependent upon an indication from the exerciser, as shown in FIG. 5B. The identification and display of the sensor(s) may be valuable from a marketing point of view, so as to link the recording gear to the results.

In an embodiment, the SCS 100 may be caused to output an audio track during the exercise presentation. The audio track may be, e.g., a music track uploaded by the exerciser to the SCS 100, or a music file automatically selected by the SCS 100 (randomly or selected to match average values of the training, such as average heart rate, average speed, average cadence, etc.). The exerciser may upload the music files from his/her device 120 by clicking the corresponding option in the user interface 112 of FIG. 5B.

In an embodiment, the SCS 100 may be configured to change one of the following based on changes in a predetermined type of exercise data: currently played audio track, beat of the currently played audio track, volume of the currently played audio track. The exerciser may select this option by clicking the corresponding option in the user interface 112 of FIG. 5B. For example, imagine that the predetermined type of exercise data is the heart rate of the exercise. Then, as the heart rate increases, the beat of the music file may be increased, and vice versa. Alternatively, as the heart rate increases above a certain threshold (e.g. given by the exerciser), the SCS 100 may change the music track to another music track or increase the volume, for example. This may improve the user experience as the music indicates the current heart rate.

In an embodiment, the SCS 100 is caused to acquire information of weather conditions at the time and location of the recorded exercise. These may be fetched from the network, e.g. from any weather-related website. Alternatively, the weather information may be obtained from the exerciser manually. Weather conditions may include temperature, wind and/or rain information at the exercise location, for example. Thereafter, the exercise presentation may further comprise displaying the weather conditions on the display 126. This may be beneficial when the current exercise is compared to another exercise on the same route performed at a different time.

In an embodiment, although not shown in FIGS. 6A to 6D, the dynamic exercise presentation may further comprise showing other information to the viewer. Such other information may include, e.g., artist and song listened when the training was recorded, comments and messages received during the training via social media (e.g. Facebook or Twitter) or web, services applied (e.g. Polar Flow), the name(s) of village(s) or city(/ies) visited during the training, exercise data curve(s) (such as heart rate (HR), speed, cadence, power, altitude, etc.) shown as chart in relation to time or distance. The data selection may be made manually by the exerciser or the viewer, or automatically based on the type of sport performed, or triggered by a predefined changes in the recorded exercise or location data (for example uphill, downhill, turn, speed-up, etc.).

Figure 6D:
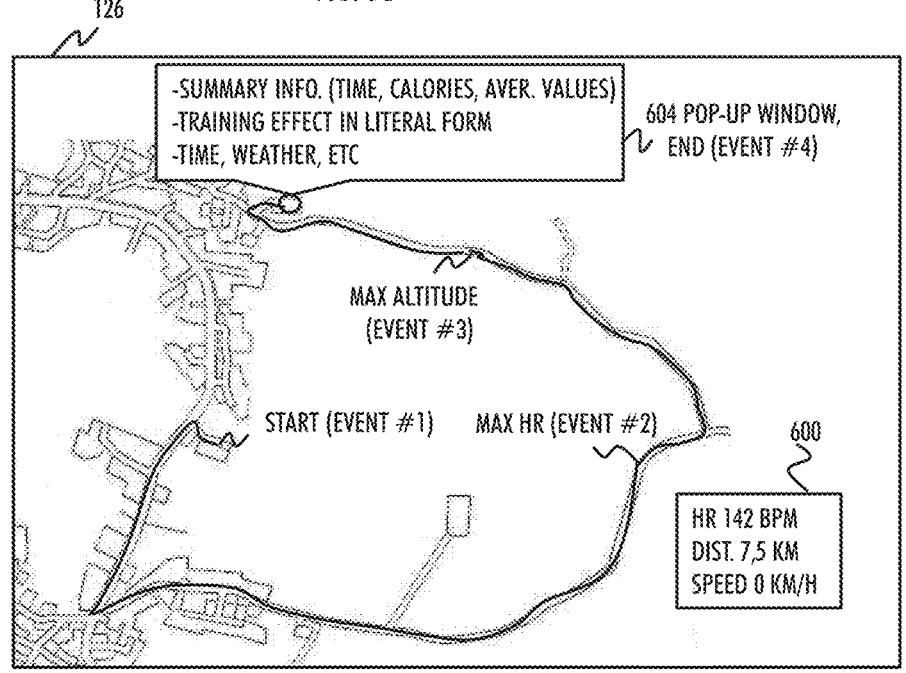

In an embodiment, the SCS 100 may determine summary information of the exercise on the basis of the exercise data and the location data. Such summary information may be displayed as values or graphs, for example. The summary information may comprise, e.g., total elapsed time, total distance, total amount of burned calories, time or distance division to a predefined HR, speed, or power zones. Then, the exercise presentation may further comprise displaying the summary information on the display 126 at the end of the exercise presentation. The summary information may be presented in the pop-up window 604, as shown in FIG. 6D, or in a separate window, for example In an embodiment, the SCS 100 may acquire, such as determine or receive, a training effect (also known as a training benefit) for the exercise on the basis of the exercise data and the location data. Thereafter, the exercise presentation may further comprise displaying a description of the training effect on the display 126 at the end of the exercise. In an embodiment, the training effect description is given in a literal form.

In an embodiment, the SCS 100 may receive an indication that the exercise presentation is to be shared in the network. Such indication may be acquired from the exerciser via the user interface 112 of FIG. 5B. The sharing may also be detailed in the user interface 112, such as by ticking whether or not the sharing is to made in the Facebook® and/or in the Twitter®, or in any other social media. As a further option, the option to share the exercise presentation in the network may be given at the end of the exercise presentation, when the exercise presentation is viewed by the user device 120 of the exerciser (detectable from the IP address of the device 120, for example).

Thereafter, the SCS 100 may share the exercise presentation in the network. After the sharing, the SCS 100 may start detecting when the shared exercise presentation is viewed over the network. In an embodiment, the SCS 100 may transmit an indication to the user device 120 when the shared exercise presentation is viewed. In an embodiment, the SCS 100 may determine the total number the exercise presentation has been viewed, as shown in FIG. 5B.

In an embodiment, the SCS 100 may further cause a display of a second exercise presentation of a second exercise on the same display 126 simultaneously with the first exercise presentation. The first exercise presentation may here denote the exercise presentation which is shown in FIGS. 6A to 6D, for example. The second exercise presentation may be generated in the same manner as the first exercise presentation. The second exercise may comprise at least a portion of the same traveled route as the first exercise and may be based on recorded second exercise data and recorded second location data.

In an embodiment, the two recorded exercises are performed at different start times.

In an embodiment, the two recorded exercises are performed by the same exerciser. In such case, there may be an option in the user interface 112 to upload the new exercise to the SCS 100, or to let the SCS 100 know that the SCS 100 may automatically combine another exercise of the same exerciser to the first exercise presentation.

In another embodiment, the second exercise is performed by another exerciser (e.g. based on another user account). This may allow a virtual race to take place.

In an embodiment, the second exercise takes place at different places within the same map background.

In an embodiment, the SCS 100 may detect whether or not an exerciser provides location data corresponding to the route traveled during the first exercise to the web service 110. The first exerciser may give an indication to the SCS 100 to perform the detection, or the SCS 100 may perform the detection automatically. Such indication may be given via the user interface 112, for example. The SCS 100 may, e.g., compare the location data units of the two exercises together (with an error margin) to detect with a reasonable probability that the two locations data sets correspond to the same traveled route. For example, other exerciser may have run on the other side of the road, but such location data difference may be within the error margins. Upon detecting that such location data is provided, the SCS 100 may generate the second exercise presentation on the basis of the second location data and the second exercise data, as explained. Then, the SCS 100 may inform the first exerciser that the second exercise presentation corresponding to the same route is available for combination with the first exercise presentation. The combination may comprise showing the two exercises in one presentation, for example. The first exerciser may then either decline or accept the combination of the two exercise presentations.

In an embodiment, the SCS 100 is caused to detect which parts of the first route of the first exercise and the second route of the second exercise overlap. It should be noted that the routes may overlap completely or that the routes may overlap only partially. Then the SCS 100 may compare parameters only during the overlap. Such compare of parameters may comprise, for example, showing predetermined event only for the part of the overlap or showing exercise data for both exercisers only during the overlap.

When multiple training are shown in one presentation, there may be two moving pointers moving along the traveled route on the display 126, each moving pointer corresponding to the locations of the first and second exerciser during the recorded exercises. As a result, there may be possibility to have a comparison or virtual race of multiple trainings performed by the same or different exercisers.

In an embodiment, when multiple trainings are shown at the same presentation, the SCS 100 may search for, e.g., the maximum heart rate among all the exercise data of all the exercises, and cause a display of only that one during the exercise presentation as one predetermined event. This may simplify the presentation, as presenting, e.g., the maximum heart rate of all the trainings may overpopulate the presentation. However, in an embodiment, the predetermined events, such as the maximum heart rates, of all the trainings are shown separately during the single exercise presentation on the display 126. This may add interest to the presentation as the differences between different exercisers or between different exercises of the same exerciser may be monitored from the display. For example, improved physical endurance may be detected when two trainings from the same exerciser show decreased heart rate at a specific location of the route.

The proposed dynamic presentation of recorded training data may be more entertaining way than the traditional presentation. Additionally, the dynamic presentation may offer a movie trailer type of ready presentation with visual details based on recorded exercise, location data and the automatically calculated highlights (i.e. the predetermined events). People watching the presentation need not do anything but to start the presentation, after which the presentation may play automatically. For example, when considering that other people may watch the presentation by using social media sharing, it is advantageous that the presentation is motivating and entertaining, yet offering interesting information about the recorded training. The proposed new manner may fascinate also people who have not earlier shown any interest to training data.

In an embodiment, the duration of the dynamic exercise presentation is, in time domain, shorter than the actual exercise. For example, when the actual exercise, such as jogging, lasted for 30 minutes, the exercise presentation may last for 1 minute. Therefore, the CSC 100 may be caused to shorten the duration of the exercise presentation compared to the duration of the corresponding exercise, wherein the shortening/shrinking is based on a predetermined shrinkage ratio or factor. Thereafter, the exercise presentation having a shortened duration may be shown on the display. The shrinking may affect similarly to the acquired exercise data and to the acquired location data so that the mapping between the exercise data and the location data need not be changed.

Regarding the SCS 100 depicted in FIG. 1, the memory 104 may be implemented using any suitable data storage technology, such as semiconductor based memory devices, flash memory, magnetic memory devices and systems, optical memory devices and systems, fixed memory and removable memory.

The memory may comprise a computer program code (FROG), which may comprise a server code executable by the SCS 100 and client code (such as Hyper Text Markup Language (HTML), or a comparable mark-up language), out of which the latter may be uploaded to the client. These codes may be executed by the SCS 100 and/or by the client's device 120 and cause the SCS 100 to display the web service 110 on the user's device 120 or to display the generated dynamic exercise presentation to the user, for example.

In an embodiment, the codes may be executed as server-side scripting, which may involve embedding scripts in an HTML source code. Such server side scripting may result in a users (client's) request to the server being handled by a script running at the server-side before the server responds to the client's request. The scripts can be written in any known server-side scripting languages available, such as Java, Python or C-language. Those scripts may be executed by the operating system of the CSC 100, and the results may be served to the client by the web service 110. The CSC 100 may thus comprise computer software that may respond to the client's web browsers request. However, the web service 110 may instead directly execute the on-line scripting languages either by itself or via extension modules.

As an alternative to the server side scripting, client-side scripting may be applied in which embedded scripts, such as JavaScript or HTML, are run at the client-side in the web browser of the user's device. Such client-side scripts may be embedded within an HTML or extensible HTML (XHTML) document but they may also be contained in a separate file, to which the document (or documents) that use it make reference. Upon request, the necessary files are sent to the users computer 120 by the SCS 100 on which they reside, for example according to a Hypertext Transfer Protocol (HTTP) or a File Transfer Protocol (FTP) communication protocols. The users web browser may then execute the script, display the document, including any visible output (such as user interface 112 or the dynamic exercise presentation) according to the executed code. The client-side scripts may also contain instructions for the web browser to follow certain user actions, (e.g., clicking a button). Yet, in one embodiment, the server-side scripting may be combined with the client-side scripting.

The control circuitry 102 of the SCS 100 may comprise an exercise presentation generation circuitry 106 for generating the exercise presentation, according to any of the embodiments. The control circuitry 102 may also comprise a display control circuitry 108 for displaying the exercise presentation on a display, such as on the display 126 of the user terminal 120.

The SCS 100 may also comprise the application user interface 112 which may be projected to the exerciser's user device 120 so that the exerciser may modify the exercise presentation and give commands to the SCS 100 in the manner shown with reference to FIG. 5B.

The SCS 100 may further comprise communication interface (TRX) 109 comprising hardware and/or software for realizing communication connectivity according to one or more communication protocols. The TRX 109 may provide the apparatus with communication capabilities to access the radio access network, for example.

The user device 120 may comprise at least one processor and a memory including a computer program code, such as the client-side code downloaded from the SCS 100 and executed by the web browser of the user's device 120. The user device 120 may also comprise the display 126 and a user interface for operating the user device 120. Such user interface may comprise, for example, at least one keypad, a microphone, a touch display, a display, a speaker, etc. A TRX may also be present at the user device 120 for transfer of data via network, for example.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A training device that generates a dynamic exercise presentation, the training device comprising:
   at least one processing device and at least one memory device including instructions, wherein the at least one memory device and the instructions are configured, with the at least one processing device, to cause the training device to perform operations comprising:
   acquiring recorded exercise data, using an exercise sensor, of an exercise performed by an exerciser;
   acquiring recorded location data of the exercise, using a location sensor, wherein the location data depicts a route travelled during the exercise;
   acquiring a map of an area which comprises the travelled route;
   detecting at least one predetermined event on the travelled route;
   determining when the detected predetermined event took place during the travelled route on the basis of at least one of the recorded exercise data and user instructions;
   generating the dynamic exercise presentation on the basis of the exercise data and the location data, wherein the dynamic exercise presentation comprises:
   displaying the exercise data as a function of the location data on a display having the map as a background;
   automatically moving a pointer on the display along the travelled route on the basis of the location data such that the moving pointer depicts the location of the exerciser on the travelled route as the exercise advances;
   displaying a pop-up window on the display at the moment when the automatically moving pointer is at the location of the travelled route where the detected predetermined event took place, wherein the pop-up window comprises data associated with the detected predetermined event;
   causing a display of the exercise presentation on the display via a network; and
   causing a display of a second exercise presentation of a second exercise on the same display simultaneously with the first exercise presentation, wherein the second exercise comprises at least a portion of the same travelled route as the first exercise and is based on recorded second exercise data and recorded second location data, wherein the second exercise is performed by a different exerciser than the first exercise, wherein the exerciser performing the second exercise has a different exercise data user account than the exerciser preforming the first exercise.

2. The training device of claim 1, wherein the dynamic exercise presentation further comprises:
   displaying the route travelled on the display cumulatively as the moving pointer moves on the travelled route.

3. The training device of claim 1, wherein the moving pointer is associated with a window for showing at least some of the exercise data, wherein the exercise data to be shown on the window is based on the location data.

4. The training device of claim 1, wherein the operations further comprise:
   acquiring an indication of required content of a pop-up window associated with a predetermined event; and
   modifying the pop-up window for the predetermined event on the basis of the indication.

5. The training device of claim 1, wherein the operations further comprise:
   acquiring an indication that a pop-up window for a predetermined event is to include a street view corresponding to the location on the travelled route;
   fetching the street view; and
   including the street view to the pop-up window, and wherein the dynamic exercise presentation further comprises:
   displaying the pop-up window with the street view when the moving pointer is at the location of the particular predetermined event on the travelled route.

6. The training device of claim 1, wherein the operations further comprise:
   acquiring an indication that a pop-up window for a predetermined event is to comprise content from an indicated internet protocol address;
   fetching the content from the indicated internet protocol address; and
   including the content to the pop-up window, and wherein the dynamic exercise presentation further comprises:
   displaying the pop-up window with the content when the moving pointer is at the location of the particular predetermined event on the travelled route.

7. The training device of claim 1, wherein the operations further comprise acquiring the exercise data and the location data from a web service, wherein the web service comprises an exercise data user account associated with the exerciser.

8. The training device of claim 1, wherein the operations further comprise acquiring personal information of the exerciser from the exercise data user account, and wherein the dynamic exercise presentation further comprises displaying at least some of the personal information on the display.

9. The training device of claim 1, wherein the operations further comprise acquiring information of the at least one sensor used for recording the exercise data and/or location data from the exercise data user account, wherein the exercise presentation further comprises displaying at least some of the information of the at least one sensor on the display, the information of the at least one sensor comprising at least one of a brand, model, type of the at least one sensor.

10. The training device of claim 1, wherein the exercise presentation further comprises:
   outputting an audio track during the exercise presentation; and wherein the operations further comprise:
   changing the volume of the currently played audio track based on changes in a predetermined type of exercise data.

11. The training device of claim 1, wherein the operations further comprise acquiring information of weather conditions at the time and location of the exercise, and wherein the exercise presentation further comprises displaying the weather conditions on the display.

12. The training device of claim 1, wherein the at least one type of the exercise data shown on the display depends on the location of the moving pointer on the travelled route.

13. The training device of claim 1, wherein the operations further comprise acquiring a physiological training effect of the exercise on the exerciser on the basis of the exercise data and the location data, wherein the exercise presentation further comprises displaying a literal description of the physiological training effect on the display.

14. The training device of claim 1, wherein the operations further comprise:
   receiving an indication that the exercise presentation is to be shared on the network;
   transmitting the exercise presentation to a social media site on the network;
   detecting that the transmitted exercise presentation is viewed; and
   transmitting an indication to a device when the transmitted exercise presentation is viewed.

15. The training device of claim 1, wherein the operations further comprise:
   detecting when an exerciser provides the second location data corresponding to the same route as travelled during the first exercise;
   upon detecting that such location data is provided, generating the second exercise presentation on the basis of the second location data and the associated second exercise data; and informing the first exerciser that the second exercise presentation corresponding to the same route as in the first exercise is available to be combined to the first exercise presentation.

16. A method for generating a dynamic exercise presentation, comprising:
   acquiring recorded exercise data, using an exercise sensor, of an exercise performed by an exerciser;
   acquiring recorded location data of the exercise, using a location sensor, wherein the location data depicts a route travelled during the exercise;
   acquiring a map of an area which comprises the travelled route;
   detecting at least one predetermined event on the travelled route;
   determining when the detected predetermined event took place during the travelled route on the basis of at least one of the recorded exercise data and user instructions;
   generating the dynamic exercise presentation on the basis of the exercise data and the location data, wherein the dynamic exercise presentation comprises:
   displaying the exercise data as a function of the location data on a display having the map as a background;
   automatically moving a pointer on the display along the travelled route on the basis of the location data such that the moving pointer depicts the location of the exerciser on the travelled route as the exercise advances;
   displaying a pop-up window on the display at the moment when the automatically moving pointer is at the location of the travelled route where the detected predetermined event took place, wherein the pop-up window comprises data associated with the detected predetermined event;
   causing a display of the exercise presentation on the display via a network; and
   causing a display of a second exercise presentation of a second exercise on the same display simultaneously with the first exercise presentation, wherein the second exercise comprises at least a portion of the same travelled route as the first exercise and is based on recorded second exercise data and recorded second location data, wherein the second exercise is performed by a different exerciser than the first exercise, wherein the exerciser performing the second exercise has a different exercise data user account than the exerciser preforming the first exercise.

17. A computer program product embodied on a distribution medium readable by a computer and comprising program instructions which, when executed by an apparatus, cause the apparatus to perform operations comprising:
   acquiring recorded exercise data, using an exercise sensor, of an exercise performed by an exerciser;
   acquiring recorded location data of the exercise, using a location sensor, wherein the location data depicts a route travelled during the exercise;
   acquiring a map of an area which comprises the travelled route;
   detecting at least one predetermined event on the travelled route;
   determining when the detected predetermined event took place during the travelled route on the basis of at least one of the recorded exercise data and user instructions;
   generating the dynamic exercise presentation on the basis of the exercise data and the location data, wherein the dynamic exercise presentation comprises:
   displaying the exercise data as a function of the location data on a display having the map as a background;
   automatically moving a pointer on the display along the travelled route on the basis of the location data such that the moving pointer depicts the location of the exerciser on the travelled route as the exercise advances;
   displaying a pop-up window on the display at the moment when the automatically moving pointer is at the location of the travelled route where the detected predetermined event took place, wherein the pop-up window comprises data associated with the detected predetermined event;
   causing a display of the exercise presentation on the display via a network; and causing a display of a second exercise presentation of a second exercise on the same display simultaneously with the first exercise presentation, wherein the second exercise comprises at least a portion of the same travelled route as the first exercise and is based on recorded second exercise data and recorded second location data, wherein the second exercise is performed by a different exerciser than the first exercise, wherein the exerciser performing the second exercise has a different exercise data user account than the exerciser preforming the first exercise.

* * * * *

UNITED STATES PATENT AND TRADEMARK OFFICE
CERTIFICATE OF CORRECTION

PATENT NO. : 9,760,692 B2  
APPLICATION NO. : 14/031768  
DATED : September 12, 2017  
INVENTOR(S) : Mika Erkkila and Ville Kampman Page 1 of 1

It is certified that error appears in the above-identified patent and that said Letters Patent is hereby corrected as shown below:

On the Title Page

Item (57), In the Abstract:
Line 4: now reads "a route travlled during the"
should read --a route traveled during the--

Line 6: now reads "trivlled route; generate"
should read --traveled route; generate--

In the Specification

Column 12, Line 62: now reads "entertaining way than the"
should read --entertaining than the--

Column 13, Line 13: now reads "the CSC 100 may be caused"
should read --the SCS 100 may be caused--

Column 13, Line 30: now reads "program code (FROG), which"
should read --program code (PROG), which--

Column 13, Line 46: now reads "the CSC 100, and the results may"
should read --the SCS 100, and the results may--

Column 13, Line 47: now reads "The CSC 100 may thus comprise"
should read --The SCS 100 may thus comprise--

Signed and Sealed this  
Twenty-fourth Day of July, 2018

Andrei Iancu  
*Director of the United States Patent and Trademark Office*